United States Patent
Dury et al.

(10) Patent No.: US 6,580,007 B1
(45) Date of Patent: Jun. 17, 2003

(54) METHOD FOR PREPARING TETRAKIS (PENTAFLUOROPHENYL) BORATE DERIVATIVES

(75) Inventors: Michel Dury, Lyons (FR); Christian Priou, West Windsor (FR); Jacques Richard, Luzinay (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/762,349

(22) PCT Filed: Aug. 2, 1999

(86) PCT No.: PCT/FR99/01910
§ 371 (c)(1),
(2), (4) Date: Apr. 23, 2001

(87) PCT Pub. No.: WO00/08028
PCT Pub. Date: Feb. 17, 2000

(30) Foreign Application Priority Data

Aug. 7, 1998 (FR) ............................................. 98 10212

(51) Int. Cl.[7] ................................................. C07F 5/02
(52) U.S. Cl. ........................................................... 568/6
(58) Field of Search ...................... 568/1, 6; 260/665 R

(56) References Cited

U.S. PATENT DOCUMENTS 5,493,056 A * 2/1996 Ikeda et al. ..................... 568/6
5,600,005 A * 2/1997 Naganuma et al. ............. 568/6
5,679,289 A * 10/1997 Krafft ..................... 260/665 R

OTHER PUBLICATIONS

CA:112:245092 abs of Vesti. Akad. Navuk. BSSR, Ser. Khim. Navuk by Kulikov et al pp9–11 1990.*
CA:54:53874 abs of J Phys. CHem by Gunn et al pp 61–63 1960.*

* cited by examiner

*Primary Examiner*—Jean F. Vollano

(57) ABSTRACT

The invention concerns a novel method for preparing tetrakis(pentafluorophenyl)borate derivatives of general formula $MB(C_6F_5)_4$, M being selected among $Na^+$, $Li^+$, or $K^+$, wherein: (a) a $C_6F_5X$ solution, X being selected among H, Cl, Br or I, in anhydrous butylic ether is contacted with an alkyllithium, the mol ratio of $C_6F_5X$/alkyllithium being 1 to 1.1, and the alkyl radical, linear or branched comprising 1 to 10 carbon atoms; (b) the resulting product is contacted with previously non-dissolved $BR_3$, R, identical or different being selected among a chlorine atom, a fluorine atom, a bromine atom, an alkoxy radical comprising between 1 and 4 carbon atoms.

3 Claims, No Drawings

METHOD FOR PREPARING TETRAKIS (PENTAFLUOROPHENYL) BORATE DERIVATIVES

This application is an application under 35 U.S.C. Section 371 of International Application Number PCT/FR99/01910 filed on Aug. 02, 1999.

A subject matter of the present invention is a novel process for the preparation of tetrakis(pentafluorophenyl) borate derivatives.

The borate derivatives obtained according to the invention are products of use as intermediates in the preparation of catalysts for crosslinking and/or for polymerizing by the thermal route, by the photochemical route and/or under an electron beam.

These intermediates can also be used to prepare catalysts of Ziegler-Natta type for the polymerization of olefins, such as those disclosed, for example, in the documents WO 9412547 and EP-A-277 004.

In recent years, numerous documents have been published relating to the use of the polymerization catalysts obtained from tetrakis(pentafluorophenyl)borate derivatives. Mention will in particular be made, by way of examples, of the Patents EP 562 897 and EP 56 922 from Rhodia Chimie.

Other documents relate to the preparation of tetrakis (pentafluorophenyl)borate derivatives. For example, the document EP 604 961 discloses access to the borates $MB(C_6F^5)_4$ by the magnesium derivative route and the document EP 608 563 discloses access to the product $LiB(C_6F_5)_4$ from pentafluorobenzene in solution in ethyl ether.

However, the processes, in particular industrial processes, disclosed in the literature are not satisfactory. In particular, the use of an organomagnesium derivative does not allow a high yield to be obtained from the reaction for the conversion of $BR_3$, more specifically $BCl_3$, to $B(C_6F_5)_4^-$. Likewise, the use of solvents, such as ethyl ether or isopropyl ether, does not allow the industrial processes to be optimized in terms of reaction time and of yield of final product. By way of example, the use of boron trichloride in the gaseous form cannot be envisaged with ethyl ether or isopropyl ether. This is because the $BCl_3$ forms, with these ethers, relatively stable complexes which do not react to any extent with the compound $LiC_6F_5$.

A subject matter of the present invention is a novel optimized process for the preparation of tetrakis (pentafluorophenyl)borate derivatives which makes it possible to landings the abovementioned disadvantages.

Among the numerous advantages of this novel process, the purity of the tetrakis(pentafluorobenzene)borate derivatives and in particular of potassium tetrakis (pentafluorobenzene)borate is improved. In addition, the novel process generates only a very small amount of $B(C_6F_5)_3$ byproduct.

Thus, a novel process for the preparation of tetrakis (pentafluorophenyl)borate of general formula $MB(C_6F_5)_4$ (I), M being chosen from Na$^+$, Li$^+$ or K$^+$, has thus now been developed, in which process:

(a) a solution of $C_6F_5X$, X being chosen from H, Cl, Br and I, in anhydrous butyl ether is brought into contact with an alkyllithium, the $C_6F_5X$/alkyllithium molar ratio being between 1 and 1.1 and the alkyl radical being chosen from linear or branched radicals comprising from 1 to 10 carbon atoms and preferably a hexyl radical;

(b) the resulting product is brought into contact with $BR_3$ (II), undissolved beforehand before its use, R, which is identical or different, being chosen from a chlorine atom, a fluorine atom, a bromine atom and an alkoxy radical comprising from 1 to 4 carbon atoms.

$BR_3$ used thus makes it possible to dispense with a conditioning stage before its introduction. This direct use of $BR_3$ greatly improves the reaction rate within the mixture (direct contacting).

Furthermore, the choice of anhydrous butyl ether as solvent and of $BR_3$ makes it possible to avoid the formation of complexes which may be stable and harmful to the reactivity of the products employed in the preparation process.

According to a first specific form of the invention, $BR_3$ is advantageously introduced into the reaction mixture in the gaseous form.

According to a second specific form of the invention, $BR_3$ is boron trichloride.

Mention will be made, as examples of other $BR_3$ (II) products, of $BF_3.OEt_2$, $B(OMe)_3$, $BBr_3$, and the like.

As an example of an industrial preparation process according to the invention, the stages below are followed for the preparation of potassium tetrakis(pentafluorophenyl) borate:

(a) the anhydrous butyl ether and the pentafluorobenzene are introduced into the reactor and are then mixed with stirring while cooling to a temperature of approximately −70° C., (b) a solution of alkyllithium and preferably of hexyllithium is run into the reaction mixture at a controlled rate, (c) undissolved $BR_3$, preferably boron trichloride, is then added to the reaction mixture and the mixture is allowed to rise to a temperature in the region of 0° C., (d) an aqueous potassium chloride solution is then introduced, the mixture subsequently being stirred at ambient temperature, (e) after separating by settling, the aqueous phase is withdrawn and a potassium chloride solution is added before distilling under a reduced pressure, preferably of less than 500 mbar, (f) after filtering and optionally washing, the tetrakis (pentafluorophenyl)borate derivative of general formula $KB(C_6F_5)_4$ is recovered.

EXAMPLES

The following examples are given by way of illustration. They make it possible in particular to achieve a better understanding of the invention and to emphasize some of the advantages and to glimpse some one of the alternative implementational forms.

The Preparation Examples 1 and 2 are preparation processes according to the invention and Example 3 is a preparation process given by way of comparison.

Example 1

The following:

200 ml of anhydrous butyl ether (Aldrich), 36 g of pentafluorobenzene (Fluorose), are charged to a 0.7 l jacketed homothetic reactor equipped with a Rushes turbine and carefully inert with argon.

The mixture is stirred and cooled to a temperature of −70° C. by circulating acetone cooled with dry ice.

56.8 g of a 33% solution of hexyllithium in hexane (Chemetall) are then run in via a dropping funnel. The time for the introduction is 20 min and the temperature of the reaction mass changes between −70° C. and −63° C.

This mixture is stirred for 20 min. The temperature falls back to −70° C. 49.5 ml of a 1 M solution of boron trichloride in heptane (Aldrich) are added dropwise to the reaction mass. The mixture is subsequently left to stir for 10 min and then the circulating liquid coolant is cut off.

The temperature of the mixture rises to approximately 0.5° C., at which temperature 250 ml of a 25% solution of KCl in water are added. The temperature changes from 0.5° C. to 17° C. during the addition. The stirring rate is increased. The mixture is stirred for 2 h at ambient temperature and then stirring is halted. The reaction mass is separated by settling. The aqueous phase (246 ml) is withdrawn.

The organic phase remaining in the reactor is stirred and the dropping funnel is replaced with a Vigreux return column, a separator and a 500 ml collecting flask. 250 ml of the 25% aqueous KCl solution are charged.

The jacket of the reactor is heated to a temperature of 85° C. and the pressure inside the apparatus is reduced to approximately 200 mbar. The organic solvents are distilled off without exceeding a temperature of 76° C. in the reaction mass. After having distilled off 275 ml of reaction mixture (including 60 ml of water), the appearance of a white precipitate of $KB(C_6F_5)_4$ is observed.

The entire setup is brought back to atmospheric pressure. 60 ml of water and 50 ml of toluene are added to the reaction mass.

After having set the pressure in the apparatus at approximately 200 mbar, distillation is continued.

45 ml of distillate are recovered. The pressure in the apparatus is brought back to atmospheric pressure and then the reaction mass is cooled to a temperature of 35° C.

The potassium tetrakis(pentafluorophenyl)borate precipitates. It is recovered by filtering through a No. 3 sintered glass funnel. Washing with 100 ml of rinsing water from the reactor is carried out. The white solid obtained is dried for 16 h at a temperature of 50° C. under a vacuum of 20 mbar.

34.4 g of potassium tetrakis(pentafluorophenyl)borate are recovered, i.e.:

a yield of 96.8% with respect to the $BCl_3$ charged, a yield of 89.4% with respect to the pentafluorobenzene charged.

The analytical characteristics of the product obtained are found in Table 1.

Example 2

The following:

200 ml of anhydrous butyl ether (Aldrich), 36 g of pentafluorobenzene (Fluorochem), are charged to a 0.7 l jacketed homothetic reactor equipped with a Rushton turbine and carefully inerted with argon.

The mixture is stirred and cooled to a temperature of −70° C. by circulating acetone cooled with dry ice.

56.8 g of a 33% solution of hexyllithium in hexane (Chemetall) are then run in via a dropping funnel. The time for the introduction is 20 min and the temperature of the reaction mass changes between −70° C. and −63° C.

This mixture is stirred for 20 min. The temperature falls back to −70° C. 5.8 g of gaseous boron trichloride are introduced over 5 min using a dip pipe. The mixture is subsequently left to stir for 10 min and then the circulating liquid coolant is cut off.

The temperature of the reaction mixture rises to a temperature of approximately 0.5° C., at which temperature 250 ml of a 25% solution of KCl in water are added.

The temperature changes from 0.5° C. to 17° C. during the addition. The stirring rate is increased. The mixture is stirred for 2 h at ambient temperature and then stirring is halted. The reaction mass is separated by settling. The aqueous phase (246 ml) is withdrawn.

The organic phase remaining in the reactor is stirred and the dropping funnel is replaced with a Vigreux return column, a separator and a 500 ml collecting flask.

250 ml of the 25% aqueous KCl solution are charged.

The jacket of the reactor is heated to a temperature of 85° C. and the pressure inside the apparatus is reduced to 200 mbar. The organic solvents are distilled off without exceeding a temperature of 76° C. in the reaction mass. After having distilled off 275 ml of reaction mixture (including 60 ml of water), the appearance of a white precipitate of $KB(C_6F_5)_4$ is observed.

The entire setup is brought back to atmospheric pressure. 60 ml of water and 50 ml of toluene are added to the reaction mass.

After having set the pressure in the apparatus at 200 mbar, distillation is continued.

45 ml of distillate are recovered. The pressure in the apparatus is brought back to atmospheric pressure and then the reaction mass is cooled to a temperature of 35° C.

The potassium tetrakis(pentafluorophenyl)borate precipitates. It is recovered by filtering through a No. 3 sintered glass funnel. Washing with 100 ml of rinsing water from the reactor is carried out. The white solid obtained is dried for 16 h at a temperature of 50° C. under a vacuum of 20 mbar.

33.22 g of potassium tetrakis(pentafluorophenyl)borate are recovered, i.e.:

a yield of 93.5% with respect to the $BCl_3$ charged, a yield of 86.4% with respect to the pentafluorobenzene charged.

The analytical characteristics of the product obtained are found in Table 1.

Example 3

The following:

200 ml of anhydrous isopropyl ether (Aldrich), 36 g of pentafluorobenzene (Fluorochem), are charged to a 0.7 l jacketed homothetic reactor equipped with a Rushton turbine and carefully inerted with argon.

The mixture is stirred and cooled to a temperature of −70° C. by circulating acetone cooled with dry ice. 56.8 g of a 33% solution of hexyllithium in hexane (Chemetall) are then run in via a dropping funnel. The time for the introduction is 20 min and the temperature of the reaction mass changes between −70° C. and −63° C.

This mixture is stirred for 20 min. The temperature falls back to −70° C. 47.3 ml of a 1 M solution of boron trichloride in heptane (Aldrich) are added dropwise to the reaction mass. The mixture is subsequently left to stir for 10 min and then the circulating liquid coolant is cut off. The temperature of the mixture rises to approximately 0.5° C., at which temperature 250 ml of a 25% solution of KCl in water are added. The temperature changes from 0.5° C. to 17° C. during the addition. The stirring rate is increased. The mixture is stirred for 2 h at ambient temperature and then stirring is halted.

The reaction mass is separated by settling. The aqueous phase (246 ml) is withdrawn.

The organic phase remaining in the reactor is stirred and the dropping funnel is replaced with a Vigreux return column, a separator and a 500 ml collecting flask.

250 ml of the 25% aqueous KCl solution are charged.

The jacket of the reactor is heated to a temperature of 85° C. and the pressure inside the apparatus is reduced to approximately 200 mbar. The organic solvents are distilled off without exceeding a temperature of 76° C. in the reaction mass. After having distilled off 275 ml of reaction mixture (including 60 ml of water), the appearance of a white precipitate of KB $(C_6F_5)_4$ is observed.

The entire setup is brought back to atmospheric pressure. 60 ml of water and 50 ml of toluene are added to the reaction mass.

After having set the pressure in the apparatus at 200 mbar, distillation is continued.

45 ml of distillate are recovered. The pressure in the apparatus is brought back to atmospheric pressure and then the reaction mass is cooled to a temperature of 35° C.

The potassium tetrakis(pentafluorophenyl)borate precipitates. It is recovered by filtering through a No. 3 sintered glass funnel. Washing with 100 ml of rinsing water from the reactor is carried out. Two washing operations with 30 ml of toluene are subsequently carried out. The white solid obtained is dried for 16 h at a temperature of 50° C. under a vacuum of 20 mbar.

30.1 g of potassium tetrakis(pentafluorophenyl)borate are recovered, i.e.:

a yield of 88.6% with respect to the $BCl_3$ charged, a yield of 80.8% with respect to the pentafluorobenzene charged.

The analytical characteristics of the product obtained are found in Table 1.

Example 4

A 4000 ml four-necked round-bottomed flask equipped with a mechanical stirrer, a water-cooled condenser, a thermometer and a dropping funnel is used. The setup is dried beforehand under an argon atmosphere and then anhydrous heptane (1600 ml) and bromopentafluorobenzene (151.7 g, 0.614 mol) are charged.

The combined mixture is stirred and is cooled to –75° C. using an acetone/dry ice bath. Butyllithium (1.6 M solution in hexane, 373 ml) is charged to the dropping funnel and is added dropwise over 50 minutes.

The mixture is subsequently left to stir for hours at a temperature of –78° C. Boron trichloride (1 M solution in hexane, 149 ml) is charged to the non-cooled dropping funnel and is added over thirty minutes. The cooling bath is removed and the reaction mixture is allowed to return to ambient temperature.

The reaction mixture is subsequently left to stir for 12 hours. A saturated-aqueous KCl solution (180 g in 750 ml of water) is added dropwise and then the mixture is left to stir for two hours.

The reaction mixture is filtered and the filtrate is washed with a saturated KCl solution and is then dried at a temperature of 40° C. under a vacuum of 1 mm Hg.

The potassium tetrakis(pentafluorophenyl)borate is recovered in the form of a white powder.

The analytical characteristics of the product obtained are found in Table 1.

TABLE 1

|  | Example 1 | Example 2 | Example 3 | Example 4 |
|---|---|---|---|---|
| Yield/BCl3 (%) | 96.8 | 93.5 | 88.6 | 92 |
| Yield/$C_6H_5H$ (%) | 89.4 | 86.4 | 80.8 | / |
| NMR analysis (molar %) |  |  |  |  |
| $KB(C_6F_5)_4$ | >99 | 98 | 96 | 95 |
| $KB(C_6F_5)_3OH$ | 0 | 2 | 1 | 3 |
| HPLC analysis (wgt %) |  |  |  |  |
| $KB(C_6F_5)_4$ | 94 | 96 | 95 | / |
| $KB(C_6F_5)_3OH$ | 0.5 | 0.5 | 0.8 | / |
| $H_2O$ (wgt %) | 2.71 | 2.52 | 2.50 | / |
| Cl (wgt %) | 0.05 | 0.2 | 0.1 | / |

What is claimed is:

1. A process for the preparation of potassium tetrakis (pentafluorobenzene)borate in a reactor, comprising the following steps:

(a) adding anhydrous butyl ether and pentafluorobenzene into the reactor to obtain a reaction mixture, and, then, mixing with stirring the reaction mixture while cooling to a temperature of about –70° C., to obtain a step (a) reaction mixture, (b) running a solution of alkyllithium into the step (a) reaction mixture at a controlled rate, to obtained a step (b) reaction mixture, (c) adding $BR_3$, undissolved beforehand, to the step (b) reaction mixture, wherein the R groups, identical or different, are a chlorine atom, a fluorine atom, a bromine atom or an alkoxy radical comprising between 1 and 4 carbon atoms, and rising the temperature to about 0° C., to obtain a step (c) reaction mixture, (d) adding an aqueous potassium chloride solution to the step (c) reaction mixture, and then stirring at ambient temperature, to obtain a step (d) reaction mixture, (e) settling the step (d) reaction mixture to obtain an aqueous phase and an organic phase, withdrawing said aqueous phase, adding a potassium chloride solution to the organic phase and, then, distilling the organic phase under a reduced pressure, to obtain potassium tetrakis (pentafluorophenyl)borate, and (f) recovering after filtering the potassium tetrakis (pentafluorophenyl)borate obtained in step (e).

2. The process as claimed in claim 1, wherein the alkyllithium is hexyllithium.

3. The process as claimed in claim 1, wherein $BR_3$ is boron trichloride.

* * * * *